(12) United States Patent
Ridler et al.

(10) Patent No.: US 10,142,740 B2
(45) Date of Patent: Nov. 27, 2018

(54) AUDIO MONITORING OF A HEARING PROSTHESIS

(71) Applicant: Cochlear Limited, Sydney (AU)

(72) Inventors: Oliver Ridler, Sydney (AU); Ferdie Djunaedi, Sydney (AU)

(73) Assignee: Cochlear Limited, Macquarie University, NSW (AU)

(*) Notice: Subject to any disclaimer, the term of this patent is extended or adjusted under 35 U.S.C. 154(b) by 561 days.

(21) Appl. No.: 13/915,819

(22) Filed: Jun. 12, 2013

(65) Prior Publication Data

US 2014/0270212 A1 Sep. 18, 2014

Related U.S. Application Data

(60) Provisional application No. 61/794,481, filed on Mar. 15, 2013.

(51) Int. Cl.
*H04R 25/00* (2006.01)
*A61N 1/36* (2006.01)
*A61N 1/37* (2006.01)
*A61N 1/372* (2006.01)

(52) U.S. Cl.
CPC ......... *H04R 25/30* (2013.01); *A61N 1/36032* (2013.01); *A61N 1/37252* (2013.01); *H04R 2225/67* (2013.01)

(58) Field of Classification Search
CPC .... H04R 25/30; H04R 2228/67; H04R 25/00; H04R 25/70; H04R 25/554; H04R 25/558; H04R 25/505; H04R 2225/41; H04R 2225/67; H04R 29/00; H04R 29/004; A61N 1/137252; A61N 1/36032; A61N 1/36036; A61N 1/37252; A61N 1/37211; A61B 5/121
USPC ........ 381/60, 326, 56, 58, 315, 23.1; 607/57
See application file for complete search history.

(56) References Cited

U.S. PATENT DOCUMENTS

| 7,110,822 | B1 | 9/2006 | Palmer |
| 7,212,866 | B1 | 5/2007 | Griffith |
| 7,818,066 | B1 | 10/2010 | Palmer |
| 8,170,253 | B1 | 5/2012 | Lynch |
| 2004/0234089 | A1* | 11/2004 | Rembrand ............ H04R 25/30 381/312 |

(Continued)

*Primary Examiner* — Yogeshkumar Patel

(57) ABSTRACT

The present application discloses systems and methods for engaging in monitoring of audio signals received and processed by a hearing prosthesis. In accordance with one embodiment, a method includes a monitoring device detecting a trigger event, in response to the detecting, the monitoring device transmitting to a hearing prosthesis an instruction to switch transmission modes, and in response to the transmitting, the monitoring device receiving from the hearing prosthesis an audio stream. In accordance with another embodiment, another method includes a hearing prosthesis operating in a first mode, where it receives audio signals, generates stimulation commands based on the received audio signals, and transmits to an implanted device the generated stimulation commands, receiving from an external device an instruction to switch operation modes, and in response to the receiving, switching to operate in a second mode, where it receives audio signals, generates a modulated audio stream based on the received audio signals, and transmits to the external device the modulated audio stream.

19 Claims, 5 Drawing Sheets

(56) References Cited

U.S. PATENT DOCUMENTS

| | | | | |
|---|---|---|---|---|
| 2005/0036637 | A1* | 2/2005 | Janssen | H04R 25/70 |
| | | | | 381/315 |
| 2007/0147641 | A1* | 6/2007 | Platz | H04R 25/558 |
| | | | | 381/315 |
| 2007/0282394 | A1* | 12/2007 | Segel | A61N 1/36036 |
| | | | | 607/57 |
| 2008/0147144 | A1* | 6/2008 | Money | A61N 1/36032 |
| | | | | 607/57 |
| 2009/0202084 | A1* | 8/2009 | Joeng | H04R 25/30 |
| | | | | 381/60 |
| 2011/0019810 | A1* | 1/2011 | Alexandrov | H04L 12/1827 |
| | | | | 379/204.01 |
| 2011/0299697 | A1* | 12/2011 | Sawai | H04B 1/3805 |
| | | | | 381/79 |
| 2012/0177235 | A1* | 7/2012 | Solum | H04R 25/30 |
| | | | | 381/315 |
| 2012/0224705 | A1* | 9/2012 | Meskens | H04R 25/552 |
| | | | | 381/23.1 |
| 2012/0262108 | A1* | 10/2012 | Olson | A61N 1/3787 |
| | | | | 320/108 |
| 2013/0182798 | A1* | 7/2013 | Lozano | H04L 65/4084 |
| | | | | 375/340 |

* cited by examiner

Article of Manufacture 600

Program Instructions 602

- determine that a monitoring device has come into proximity of a sound processor,

- in response to the determining, causing the monitoring device to transmit to a sound processor via a wireless communication interface an instruction to switch transmission modes, and

- receiving from the sound processor an audio stream.

Computer Readable Medium 604

Fig. 6

AUDIO MONITORING OF A HEARING PROSTHESIS

BACKGROUND

Various types of hearing prostheses may provide persons with different types of hearing loss with the ability to perceive sound. Hearing loss may be conductive, sensorineural, or a combination of both. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, such as the cochlea, where sound vibrations are converted into neural signals, or any other part of the ear, auditory nerve, or brain that processes the neural signals.

Persons with some forms of conductive hearing loss may benefit from acoustic hearing aids, vibration-based hearing devices, or other such hearing prostheses. An acoustic hearing aid typically includes a small microphone to detect sound, an amplifier to amplify certain portions of the detected sound, and a small speaker to transmit the amplified sounds into the person's ear. Vibration-based hearing devices typically include a small microphone to detect sound and a vibration mechanism to apply vibrations corresponding to the detected sound to a person's bone (e.g. the skull), thereby causing vibrations in the person's inner ear, thus bypassing the person's auditory canal and middle ear. Vibration-based hearing devices include bone-anchored hearing devices, direct acoustic cochlear stimulation devices, or other vibration-based devices. A bone-anchored hearing device typically utilizes a surgically-implanted mechanism to transmit sound via direct vibrations of the skull. Similarly, a direct acoustic cochlear stimulation device typically utilizes a surgically-implanted mechanism to transmit sound via vibrations corresponding to sound waves to generate fluid motion in a person's inner ear. Other non-surgical vibration-based hearing devices may use similar vibration mechanisms to transmit sound via direct vibration of teeth or other cranial or facial bones.

Persons with certain forms of sensorineural hearing loss may benefit from cochlear implants or auditory brainstem implants. For example, cochlear implants may provide a person having sensorineural hearing loss with the ability to perceive sound by stimulating the person's auditory nerve via an array of electrodes implanted in the person's cochlea. The cochlear implant detects sound waves and converts them into a series of electrical stimulation signals that are delivered to the implant recipient's cochlea via the array of electrodes. Auditory brainstem implants may use technology similar to cochlear implants, but instead of applying electrical stimulation to a person's cochlea, auditory brainstem implants apply electrical stimulation directly to a person's brainstem, bypassing the cochlea altogether. Electrically stimulating auditory nerves in a cochlea with a cochlear implant or electrically stimulating a brainstem may enable persons with sensorineural hearing loss to perceive sound.

SUMMARY

The present disclosure sets forth systems and methods to engage in monitoring of the audio signals received and processed by a hearing prosthesis. In accordance with at least some embodiments, a method is provided that includes (i) a monitoring device detecting a trigger event, (ii) in response to the detecting, the monitoring device transmitting to a hearing prosthesis an instruction to switch transmission modes, and (iii) in response to the transmitting, the monitoring device receiving from the hearing prosthesis an audio stream.

In accordance with another embodiment, another method is provided that includes (i) a hearing prosthesis operating in a first mode, in which the hearing prosthesis receives audio signals, generates stimulation commands based on the received audio signals, and transmits to an implanted device the generated stimulation commands, (ii) the hearing prosthesis receiving from an external device an instruction to switch operation modes, and (iii) in response to the receiving, the hearing prosthesis switching to operate in a second mode, in which the hearing prosthesis receives audio signals, generates a modulated audio stream based on the received audio signals, and transmits to the external device the modulated audio stream.

In accordance with another embodiment, a monitoring device is provided that includes a wireless communication interface, an inductive element, and a processor configured for (i) determining via the inductive element that the monitoring device has come into proximity of a sound processor; (ii) in response to the determining, causing the monitoring device to transmit to the sound processor via the wireless communication interface an instruction to switch transmission modes; and (iii) receiving from the sound processor via the inductive element an audio stream.

BRIEF DESCRIPTION OF THE DRAWINGS

FIG. 6 depicts an example of an article of manufacture including computer readable media with instructions for executing functions, according to an example embodiment.

DETAILED DESCRIPTION

The following detailed description sets forth various features and functions of the disclosed systems and methods with reference to the accompanying figures. In the figures, similar symbols typically identify similar components, unless context dictates otherwise. The illustrative system and method embodiments described herein are not meant to be limiting. Certain aspects of the disclosed systems and methods can be arranged and combined in a wide variety of different configurations, all of which are contemplated herein.

Certain aspects of the disclosed systems, methods, and articles of manufacture are described herein with reference to hearing prosthesis embodiments and, more particularly, cochlear implant embodiments. However, the disclosed systems, methods, and articles of manufacture are not so limited. Many of the disclosed features and functions described with respect to the cochlear implant embodiments may be equally applicable to other embodiments that may include other types of medical stimulation prostheses, including prosthetic-limb stimulation devices, vibration-based hearing devices, direct acoustic stimulation devices, auditory brain stem implants, or any other type of medical stimulation prosthesis that is configured such that one component generates commands and transmits the commands across a data link to another component that applies or executes the commands.

Figure 1:
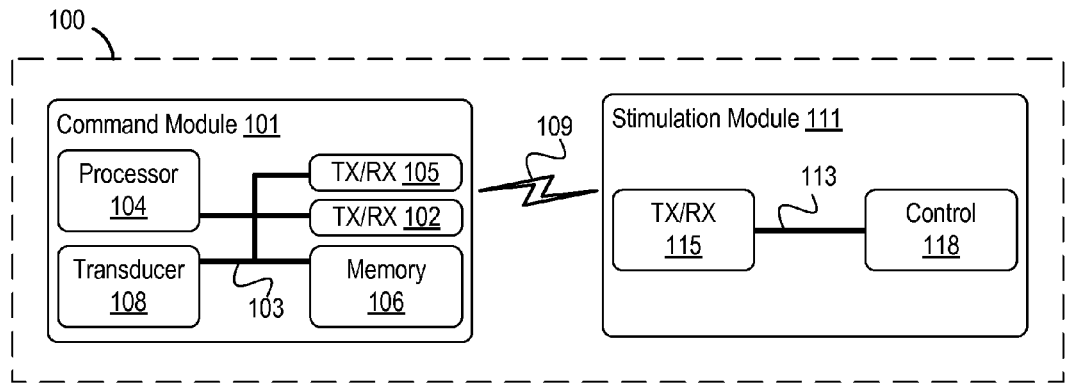
FIG. 1 depicts a block diagram of certain selected hearing prosthesis components.

FIG. 1 shows a block diagram of an example hearing prosthesis 100. The hearing prosthesis 100 may be a cochlear implant or other type of hearing prosthesis, such as a vibration-based hearing device, a direct acoustic cochlear implant, or an auditory brain stem implant. In some embodiments, hearing prostheses, such as hearing prosthesis 100, have additional or different components than those depicted in FIG. 1; but, for brevity's sake, the configuration depicted in FIG. 1 focuses on a selected set of components to help illustrate certain aspects relevant to the disclosed embodiments.

As shown in FIG. 1, hearing prosthesis 100 includes a command module 101 and a stimulation module 111. Although not shown in FIG. 1, in some embodiments, the command module 101 is included within an external component assembly that is directly or indirectly attached to the body of the hearing prosthesis recipient, while the stimulation module 111 is included within an internal component assembly that is temporarily or permanently implanted in the hearing prosthesis recipient. However, in other embodiments, the command module 101 and the stimulation module 111 are both included within one or more internal component assemblies, each of which are temporarily or permanently implanted in the hearing prosthesis recipient.

As depicted, the command module 101 includes an electromagnetic transmit/receive sub-module 102, an inductive transmit/receive module 105, a processor sub-module 104, a memory sub-module 106, and a transducer sub-module 108, all of which may be connected directly or indirectly via circuitry 103. Similarly, the stimulation module 111 includes a transmit/receive sub-module 115 and a control sub-module 118, which may be connected directly or indirectly via circuitry 113. In some prostheses, the sub-modules of the command module 101 are located on a single electronic assembly, while in others, the sub-modules of the command module 101 are spread out across two or more electronic assemblies. Likewise, the sub-modules of the stimulation module 111 may be located on a single electronic assembly or spread out across two or more electronic assemblies.

In the prosthesis shown in FIG. 1, transducer 108 is configured to detect sound waves and generate an audio signal representative of those sound waves. Transducer 108 may be further configured to transmit to processor 104, via circuitry 103, a generated audio signal that is based on the detected sound waves. Depending on the desired configuration, transducer 108 may be one or more microphones, one or more telecoil induction pickup coils, or some other sound-detection device now known or later developed.

In the prosthesis shown in FIG. 1, processor 104 is configured to receive, analyze, and encode an audio signal sent from transducer 108 (or another source) into one or more stimulation commands according to a particular sound-coding strategy. Depending on the desired configuration, processor 104 may include one or more processors, including but not limited to, programmable processors, application specific integrated circuits, programmable logic arrays, digital signal processors, and/or other general and/or special purpose processors configured to perform one or more of the functions of the hearing prosthesis 100 as described further below.

In the prosthesis shown in FIG. 1, the transmit/receive sub-modules 102 and 105 are configured to engage in transmissions from command module 101 to other devices, such as stimulation module 111 (by way of data link 109) or monitoring device 200 (see FIG. 2) (by way of data link 209). Transmit/receive sub-modules 102 and 105 are also configured to receive transmissions from other devices, such as stimulation module 111 (by way of data link 109) or monitoring device 200 (FIG. 2) (by way of data link 209). More particularly, transmit/receive sub-module 102 is configured to communicate by way of a protocol that utilizes modulation of electromagnetic radiation. Transmit/receive module 102 includes a radio-frequency (RF) interface or other wired or wireless communication interface that facilitates such data communications. Additionally, transmit/receive sub-module 105 is configured to communicate by way of a protocol that utilizes modulation of a magnetic field. Transmit/receive sub-module 105 includes a coil or other element of a transcutaneous energy transfer system along with associated circuitry to drive the coil.

Data link 109 may be any coupling that enables data transmission between the transmit/receive sub-module 105 and the transmit/receive module 115. In some prostheses, data link 109 is a transcutaneous RF inductive link. In others, data link 109 is any air interface or other wired connection. Data link 109 may be a half-duplex data link, in which the command module 101 and the stimulation module 111 do not simultaneously transmit packets. Alternatively, data link 109 is a full-duplex data link, in which the command module 101 and the stimulation module 111 are able to simultaneously transmit packets.

In the prosthesis shown in FIG. 1, memory module 106 includes one or more computer-readable storage media that can be read from, written to, or otherwise accessed by processor 104. Moreover, the storage media of memory 106 is also configured to be read from, written to, or otherwise accessed by one or more of the transmit/receive sub-module 102 and/or the transducer 108. In some cases, the storage media in the memory sub-module 106 is configured to store configuration data for the hearing prosthesis 100 or other programming instructions that facilitate general operation of the hearing prosthesis 100 in accordance with the functions described herein.

The stimulation module 111 includes a transmit/receive sub-module 115 that has functionality similar to that of transmit/receive sub-module 105. The transmit/receive sub-module 115 may be configured to receive over the data link 109 stimulation commands or other types of data transmitted by command module 101. Depending on the configuration, the transmit/receive sub-module 115 is the counterpart of transmit/receive sub-module 105 insofar as transmit/receive sub-module 115 includes an internal coil associated with the above-described transcutaneous energy transfer system. In other embodiments, stimulation module 111 includes additional transmit/receive modules (not shown) that may include an RF interface or other wired or wireless communication interface that facilitates data communications that utilize modulation of electromagnetic radiation The arrangement of transmit/receive sub-modules 105 and 115, as depicted in FIG. 1, operates to exchange messages between command module 101 and stimulation module 111. In addition, this arrangement operates to exchange messages between a fitting system (not shown) and stimulation module 111. In other embodiments, other arrangements are possible as well.

Hearing prosthesis 100 may include additional components that are not shown in FIG. 1. For example, where the hearing prosthesis 100 is a cochlear implant, the cochlear implant may include an array of two or more electrodes positioned along the recipient's cochlea. During operation, the stimulation module 111, in response to receiving one or more stimulation commands from the command module 101, applies via control sub-module 118 one or more electrical signals to the electrode array in order to stimulate the recipient's cochlea. However, as indicated above, for other types of prostheses, an electrode array, or other similar electrical or mechanical stimulation apparatus, may be positioned at or along other portions of the recipient, including for example the outer ear, inner ear, middle ear, cranial or facial bones, teeth, or brain stem.

Control sub-module 118 includes circuitry configured to control and manage the electrode array or other similar stimulation apparatus. By way of example, such circuitry may include a signal generation sub-module, a transmit amplifier sub-module, a switching sub-module, a receive amplifier sub-module, and/or a signal measurement sub-module (not shown).

Figure 2:
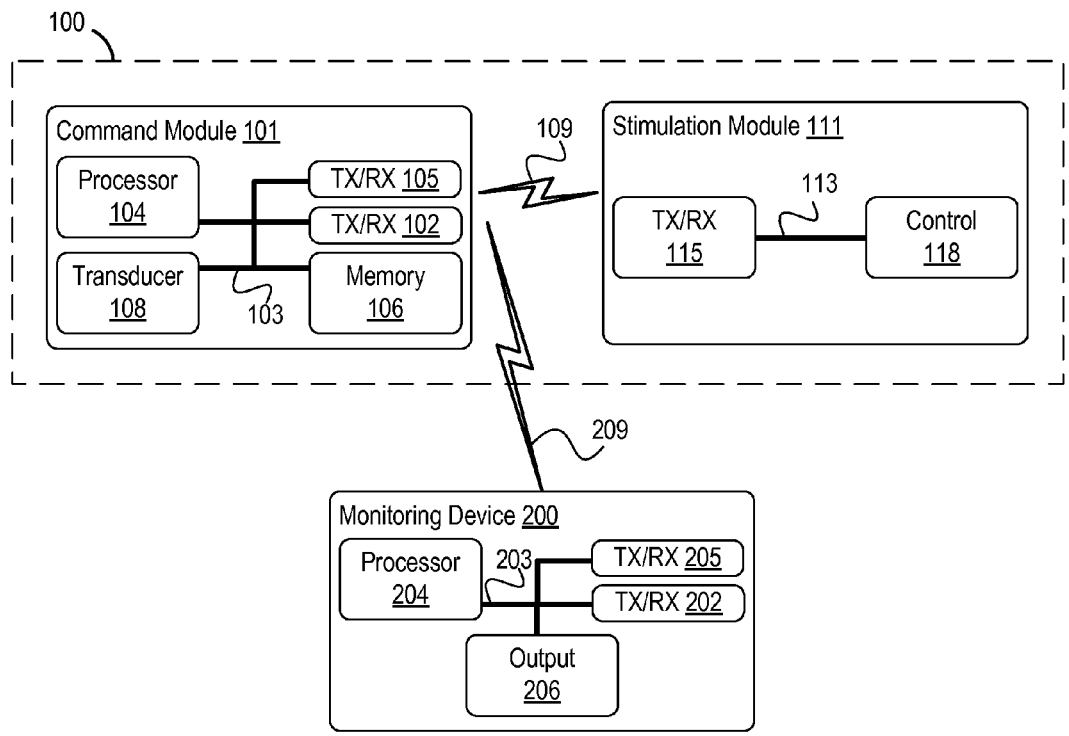
FIG. 2 depicts a block diagram of certain selected hearing prosthesis and monitoring device components, according to some embodiments of the disclosed systems and methods.

FIG. 2 depicts an example monitoring device 200, shown communicatively coupled to hearing prosthesis 100. Generally, a monitoring device is configured to communicatively couple (i.e. send/receive data) with hearing prosthesis 100. In accordance with one example use of the monitoring device 200, when monitoring device 200 comes into proximity of hearing prosthesis 100, hearing prosthesis 100 transmits to monitoring device 200 a representation of an audio stream indicative of the stimulation signal it would otherwise apply to the hearing prosthesis recipient. Typically, the monitoring device 200 is used (e.g. worn) by a person other than the hearing prosthesis recipient (e.g., an adult, when the prosthesis recipient is a child) so that such person can evaluate the characteristics of the representative audio signal and consequently make or suggest any modifications.

As depicted in FIG. 2, monitoring device 200 includes components similar to those described above with respect to command module 101 of hearing prosthesis 100. For example, monitoring device 200 includes transmit/receive sub-module 202, which is configured to communicate by way of a protocol that utilizes modulation of electromagnetic radiation, and transmit/receive sub-module 205, which is configured to communicate by way of a protocol that utilizes modulation of a magnetic field. More particularly, transmit/receive module 202 includes a radio-frequency (RF) interface or other wired or wireless communication interface that facilitates such data communications and transmit/receive sub-module 205 includes a coil or other element of a transcutaneous energy transfer system along with associated circuitry to drive the coil. As such, monitoring device 200 is configured to communicate with hearing prosthesis 100 (and more particularly, with command module 101) by utilizing the transmit/receive sub-modules 202 and 205. In accordance with the features and functionality described further herein, monitoring device 200 and hearing prosthesis 100 communicate certain signals and instructions across data link 209. Generally, data link 209 is any combination of transcutaneous data link, RF interface, or other wired or wireless communication interface that facilitates data communications for the particular employed hearing prosthesis.

Similar to processor 104, processor 204 may include one or more processors, including but not limited to, programmable processors, application specific integrated circuits, programmable logic arrays, digital signal processors, and/or other general and/or special purpose processors configured to perform one or more of the functions of the monitoring device 200. In general, the arrangement of transmit/receive sub-modules 102, 105, 202, and 205 operates to exchange instructions and other messages between processor 204 and processor 104. In other embodiments, other arrangements are possible as well.

Monitoring device 200 also includes an output interface 206, which is configured for presenting a received audio stream to a wearer of monitoring device 200. In one embodiment, the output interface 206 is a speaker or other sound-producing element; however, in other embodiments, output interface 206 is an audio jack or other interface that facilitates the connection of a portable speaker.

Example Operation

In accordance with one embodiment generally, a monitoring device that comes into proximity of a hearing prosthesis will transmit to that hearing prosthesis an instruction to begin transmitting an audio stream to the monitoring device. In response, the hearing prosthesis ceases its normal stimulation operation and begins transmitting an audio stream to the monitoring device.

Figure 3:
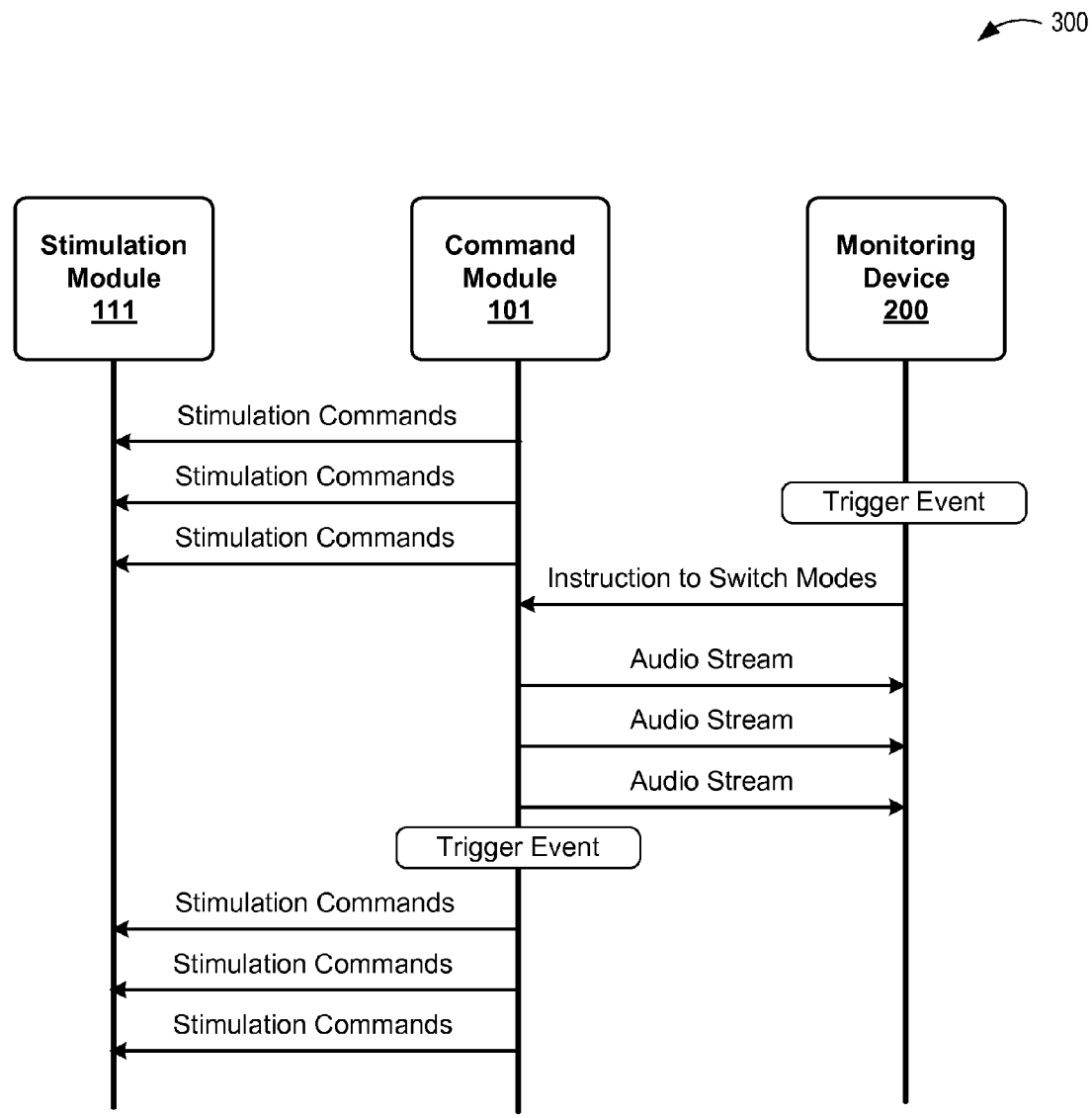
FIG. 3 depicts a message flow diagram, according to some embodiments of the disclosed systems and methods.

To help illustrate this process, reference is made to an example message flow diagram 300 depicted in FIG. 3. The message flow diagram 300 depicts an example process in accordance with at least one embodiment of the present disclosure. As depicted at the top of the message flow diagram 300, the command module 101 and stimulation module 111 of hearing prosthesis 100 are engaging in operations relating to stimulation. More particularly, command module 101 is receiving sound waves (not shown) and generating stimulation commands in accordance with a particular stimulation strategy. As depicted in the message flow diagram, command module 101 is transmitting those stimulation commands to stimulation module 111, whereupon the stimulation module applies stimulation to the prosthesis recipient in accordance with the received stimulation commands. In one embodiment, command module 101 transmits the stimulation commands to the stimulation module 111 across a transcutaneous data link via an inductive element, such as a coil.

As further depicted in the message flow diagram 300, during the stimulation operation, the monitoring device 200 encounters a trigger event. In one embodiment, the trigger event is the monitoring device 200 detecting that it has come into proximity of the command module 101. In one example of this, the monitoring device 200's inductive coil senses a modulating magnetic field as a result of communication between the command module 101's inductive coil and the stimulation module's inductive coil. In another embodiment however, the trigger event is the activation of a button on the monitoring device 200. In one example operation, a wearer of the monitoring device 200 actives a button or otherwise interacts with a user interface of the monitoring device 200 after the monitoring device 200 comes into the proximity of the command module 101. Other examples of proximity detection and trigger events are possible as well.

In response to detecting the trigger event, the monitoring device 200 transmits an instruction to the command module 101 to switch operation modes. In one embodiment, such an instruction is transmitted using a communication interface other than that used by the inductive coil. For instance, the monitoring device may transmit the instruction to the command module 101 using an RF communication interface, such as one operable at or near 2.4 GHz. However, other frequencies and other types of wireless or wired communication interfaces are possible as well.

As further depicted in the message flow diagram 300, upon receipt of the instruction, command module 101 ceases the normal stimulation operation and begins transmitting an audio stream to monitoring device 200. In one embodiment, the audio stream is a pulse width modulated (PWM) form of the sound waves received by the transducer 108 and after processing by the processor 104. In embodiments in which the hearing prosthesis 100 is a cochlear implant, the audio stream is generally representative of the sound sensation experienced by the implant recipient upon electrical stimulation by the stimulation module 111. In some embodiments, the audio stream is transmitted by the command module 101 via the inductive coil and at or around 5 MHz. Upon receipt of the audio stream, the monitoring device 200 outputs the audio stream via the output interface 206.

In some embodiments, the PWM form of the audio stream is a format unfamiliar to the stimulation module 111. Therefore, to the extent that the stimulation module 111 detects the audio stream via its inductive coil, it will not apply any stimulation to the implant recipient.

As further depicted in the message flow diagram 300, sometime during the transmission of the audio stream, the command module 101 encounters a trigger event. In some embodiments, this trigger event is a detection that the monitoring device 200 is no longer in proximity to the command module 101. For example, the command module 101 may receive periodic keep-alive pings from the monitoring device 200. When the command module 101 fails to receive a threshold number of keep-alive pings, it recognizes this failure as an indication that the monitoring device 200 is no longer in proximity to the command module 101. Other proximity detection methods are possible as well.

In other embodiments, this trigger event is the expiration of a predefined time period (e.g., one minute). And in still another embodiment, this trigger event is the receipt from the monitoring device of a message to again switch operation modes. Such a message is transmitted by the monitoring device in response to the monitoring device detecting that the monitoring device is no longer in proximity to the command module 101. However, other trigger events are possible. In any event, in response to encountering the trigger event, the command module 101 ceases the transmission of the audio stream and resumes normal stimulation operation.

Figure 4:
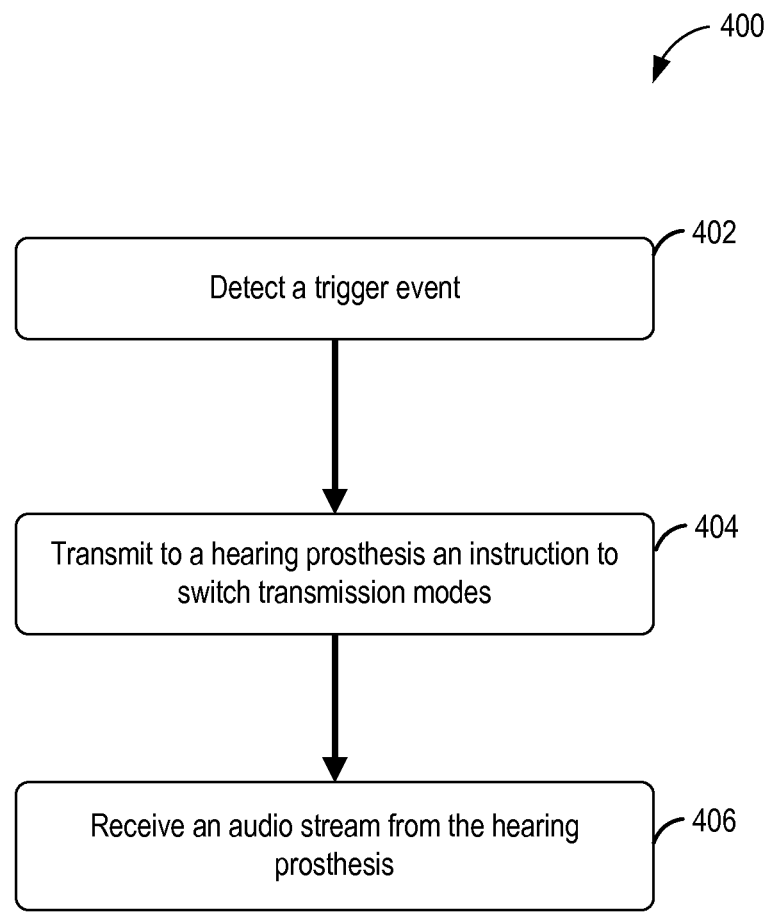
FIG. 4 depicts a flow chart depicting an example method, according to an example embodiment.

FIG. 4 is a flowchart 400 for depicting an example method for engaging in a monitoring operation. The method depicted in FIG. 4 may be executed by one or more of the modules or sub-modules of monitoring device 200. As depicted, the method begins at block 402 where a processor 204 detects a trigger event. As described above, in one embodiment, the trigger event is a detection that the monitoring device 200 has moved sufficiently close to a hearing prosthesis 100 such that near-field magnetic inductive communication can occur via an inductive coil of the monitoring device 200 and an inductive coil of the hearing prosthesis 100. More specifically, the monitoring device 200 can make this detection by recognizing when its inductive coil receives magnetic energy as a result of coming into proximity of magnetic energy transmission occurring during the normal stimulation operations of the command module 101 and stimulation module 111. In other embodiments, other ways of detecting proximity are possible as well.

In another embodiment, the trigger event is a detection of a button press on the monitoring device 200. As described above, once the wearer (or other user) of the monitoring device 200 observes that the monitoring device 200 is in proximity to the hearing prosthesis 100, the wearer may activate the monitoring operation by pressing one or more buttons associated with the monitoring device 200 or otherwise interacting with a user interface of the monitoring device 200. In other embodiments, other trigger events are possible as well.

At block 404, the processor 204, in response to detecting the trigger event, transmits to the hearing prosthesis 100 an instruction to switch transmission modes. As described above, in one embodiment, this instruction takes the form of a message transmitted via a communication protocol other than that used by the inductive coil (i.e. data link 109). For example, in one embodiment, this instruction is transmitted to the hearing prosthesis 100 via an RF communication interface operating at 2.4 GHz. However, other protocols and other ways of transmitting the instruction are possible as well.

At block 406, the monitoring device 200 receives an audio stream from the hearing prosthesis 100. As described above, in one embodiment, this audio stream is representative of the sound waves received and processed by the hearing prosthesis 100 in accordance with a particular sound coding strategy. In some embodiments, the audio stream is transmitted by the hearing prosthesis 100 to the monitoring device 200 via a communication protocol other than that used by the monitoring device 200 to transmit the instruction to switch operation modes. For example, in one embodiment, the monitoring device 200 receives the audio stream as a 5 MHz, PWM signal via the inductive coil. However, other ways of receiving the audio stream are possible as well. Although not shown in the flow chart, in some embodiments, upon receipt of the audio stream, the monitoring device 200 outputs the audio via an output interface, such as a speaker or an audio jack.

Although not shown in the flow chart, in some embodiments, when the monitoring device 200 moves away from the hearing prosthesis 100 (such that that near-field magnetic inductive communication is impaired), the monitoring device 200 transmits another instruction to the hearing prosthesis 100 to switch transmission modes. In one embodiment, this instruction to switch transmission modes is transmitted to the hearing prosthesis 100 via an RF communication interface operating at 2.4 GHz. However, other protocols and other ways of transmitting the instruction are possible as well.

Figure 5:
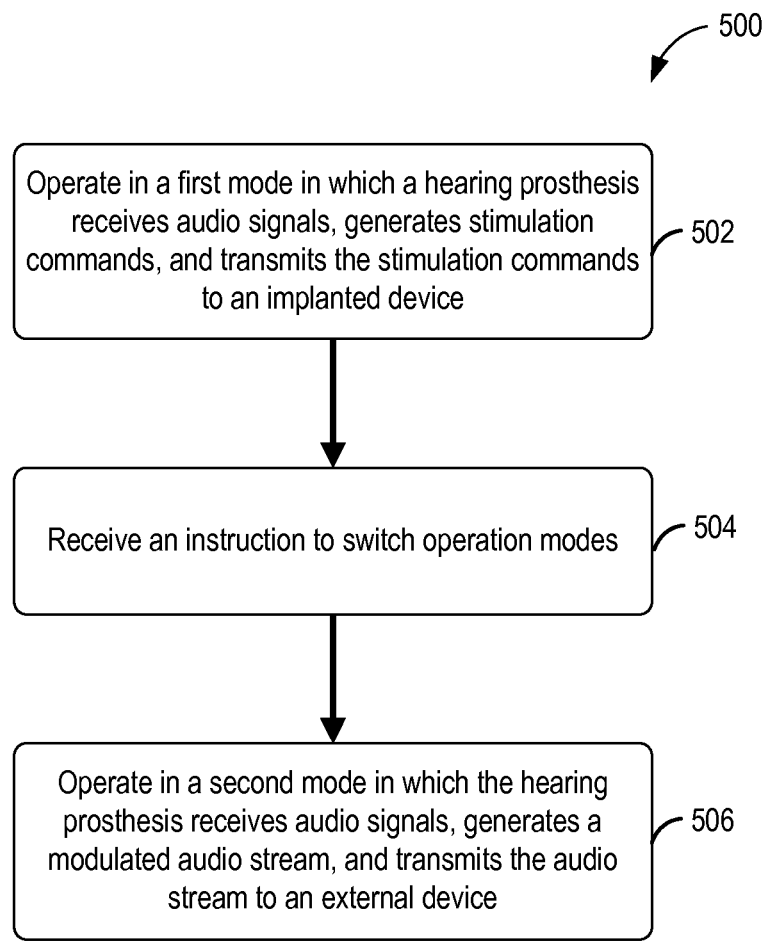
FIG. 5 depicts a flow chart depicting an example method, according to an example embodiment.

FIG. 5 is another flow chart 500 depicting an example method for switching operation modes. The method depicted in FIG. 5 may be executed by one or more of the modules or sub-modules of hearing prosthesis 100, such as processor 104. As depicted, the method begins at block 502 where a processor 104 is operating a hearing prosthesis 100 in a first operation mode in which the hearing prosthesis 100 receives audio signals, generates stimulation commands, and transmits the stimulation commands to an implanted portion of the hearing prosthesis 100. As described above, the hearing prosthesis 100 includes a command module 101, which receives the audio signals and generates stimulation commands in accordance with a stimulation strategy (sometimes referred to as a sound coding strategy), and a stimulation module 111, which receives the stimulation commands and applies some type of stimulation to the recipient in accordance with the received stimulation commands. In one embodiment, communication of the stimulation commands from the command module 101 to the stimulation module 111 occurs via a transcutaneous inductive link. However, in other embodiments, such communication occurs via other protocols and other interfaces.

At block 504, the processor 104 receives an instruction to switch operation modes. As described above, this instruction is transmitted by a monitoring device 200, in accordance with one example embodiment. In some embodiments, this instruction is received over an air interface other than the one used by the command module 101 to transmit stimulation commands to the stimulation module 111. For instance, in one embodiment, the instruction is received by the hearing prosthesis 100 over an RF communication interface operable at or around 2.4 GHz. However, in other embodiments, the instruction is received via other interfaces and using other protocols.

Finally, at block 506, the processor 104 transitions to operate the hearing prosthesis 100 in a second operation mode in which the hearing prosthesis 100 receives audio signals, generates a modulated audio stream, and transmits the audio stream to an external device (e.g. the monitoring device 200). As described above, in one embodiment, the audio stream is representative of the audio signals received and processed by the command module 101 of a hearing prosthesis 100. In some embodiments, the hearing prosthesis 100 transmits the audio stream via a communication protocol and interface other than that used by the hearing prosthesis 100 to receive the instruction to switch operation modes. For example, in one embodiment, the hearing prosthesis 100 transits the audio signal as a 5 MHz, PWM signal using the inductive coil. However, in other embodiments, other communication protocols and interfaces as possible as well.

Computer Readable Media Implementations

In some embodiments, the disclosed features and functions of the systems, methods, and algorithms shown and described herein may be implemented as computer program instructions encoded on computer readable media in a machine-readable format.

FIG. 6 depicts an example of an article of manufacture 600 including computer readable media with instructions for engaging in a monitoring operation, according to some embodiments of the disclosed systems and methods. For example, the instructions may include computer program instructions 602 for executing a computer process on a computing device.

In some implementations, the article of manufacture 600 includes a non-transitory computer readable medium 604, such as, but not limited to, a hard disk drive, a Compact Disc (CD), a Digital Video Disk (DVD), a digital tape, flash memory, etc. The one or more programming instructions 602 may be, for example, computer executable and/or logic implemented instructions stored on the computer readable medium 604. In some embodiments, processor 104 of hearing prosthesis 100 or processor 204 of monitoring device 200 is configured to perform various operations, functions, or actions to implement the features and functionality of the disclosed systems and methods based at least in part on the example programming instructions 602 as well as other functions described herein.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method comprising:
    a monitoring device detecting a trigger event, wherein the triggering event comprises detecting that the monitoring device is in a proximity of a hearing prosthesis;
    in response to the detecting that the monitoring device is in the proximity of the hearing prosthesis, the monitoring device transmitting, to the hearing prosthesis, an instruction to switch from a first mode of operation in which the hearing prosthesis generates, from first received audio signals, stimulation commands for use in stimulation of a recipient of the hearing prosthesis to a second mode of operation in which the hearing prosthesis ceases generation of stimulation commands and instead generates, from second received audio signals, an audio stream for transmission to the monitoring device, wherein the monitoring device is separate from the hearing prosthesis; and
    the monitoring device receiving from the hearing prosthesis an audio stream based on the second audio signals received by the hearing prosthesis.

2. The method of claim 1, wherein the detecting that the monitoring device is in a proximity of the hearing prosthesis comprises:
    the monitoring device determining that an inductive element of the monitoring device is sufficiently close to an inductive element of the hearing prosthesis.

3. The method of claim 1, wherein the transmitting of the instruction to switch transmission modes occurs via a first wireless communication protocol, and wherein the receiving of the audio stream occurs via a second wireless communication protocol.

4. The method of claim 3, wherein the first wireless communication protocol is a protocol operable via modulation of electromagnetic radiation, and wherein the second wireless communication protocol is a protocol operable via modulation of a magnetic field.

5. The method of claim 3, further comprising:
    the monitoring device detecting that an inductive element of the monitoring device is no longer sufficiently close to an inductive element of the hearing prosthesis; and
    in response to the detecting, the monitoring device transmitting another instruction, to the hearing prosthesis, instructing the hearing prosthesis to switch from the second mode of operation back to the first mode of operation, wherein the transmitting of the another instruction to switch transmission modes occurring via the first wireless communication protocol.

6. The method of claim 1, further comprising:
    in response to the receiving, the monitoring device amplifying the audio stream and outputting the audio stream via an output interface of the monitoring device.

7. A method comprising:
    receiving a first set of audio signals at a hearing prosthesis;
    operating the hearing prosthesis in a first mode in which the hearing prosthesis generates stimulation commands based on the first set of audio signals and transmits the stimulation commands to an implanted device;
    at the hearing prosthesis, receiving from an external device, an instruction to switch from operating in the first mode to operating in a second mode;
    receiving a second set of audio signals at the hearing prosthesis;
    operating the hearing prosthesis in the second mode in which the hearing prosthesis ceases generation of stimulation commands and instead generates a modulated audio stream based on the second set of received audio signals and transmits the modulated audio stream to the external device without transmitting the modulated audio stream to the implanted device, wherein the instruction to switch to operating in the second mode is received via a first wireless communication protocol operable via modulation of electromagnetic radiation.

8. The method of claim 7, wherein the hearing prosthesis comprises a sound processor of a cochlear implant system, and wherein the implanted device comprises an electrode array of the cochlear implant system.

9. The method of claim 7,
wherein the hearing prosthesis receiving from the external device the instruction to switch to operating in the second mode comprises the hearing prosthesis receiving the instruction in accordance with the first wireless communication protocol, and wherein in the first mode the hearing prosthesis transmits the stimulation commands to the implanted device in accordance with a second wireless communication protocol that is different from the first wireless communication protocol.

10. The method of claim 9,
wherein the first wireless communication protocol is a wireless communication protocol operable at or near 2.4 GHz, and
wherein the second wireless communication protocol is a protocol operable via magnetic induction at or near 5 MHz.

11. The method of claim 7, further comprising:
the hearing prosthesis detecting that the external device is not in proximity to the hearing prosthesis; and
in response to the detecting, the hearing prosthesis switching from operating in the second mode to operating in the first mode.

12. The method of claim 11, wherein the detecting comprises the hearing prosthesis determining that an inductive element of the external device is not sufficiently close to an inductive element of the hearing prosthesis.

13. The method of claim 11, wherein the detecting comprises the hearing prosthesis receiving from the external device another instruction to switch operation modes, the another instruction being transmitted by the external device in response to the external device determining that an inductive element of the external device is no longer sufficiently close to an inductive element of the hearing prosthesis.

14. A command module of a hearing prosthesis, comprising:
at least one transducer configured to receive sound signals;
a first transmit/receive sub-module;
a second transmit/receive sub-module; and
at least one processor configured to:
operate in a first mode to generate stimulation commands based on a first set of audio signals received at the at least one transducer and to transmit the stimulation commands to a stimulation module of the hearing prosthesis via the first transmit/receive sub-module,
receive, from an external device, an instruction to switch from the first mode to a second mode, and
in response to receiving the instruction, operate in the second mode to generate an audio stream based on a second set of received audio signals received at the at least one transducer and to transmit the audio stream to an external device via the second transmit/receive sub-module without transmitting the audio stream to the implanted device.

15. The command module of claim 14, wherein the instruction to switch to the second mode is received via a wireless communication protocol operable via modulation of electromagnetic radiation.

16. The command module of claim 14, wherein the first transmit/receive module operates in accordance with a first wireless communication protocol, while the second transmit/receive module operates in accordance with a second wireless communication protocol that is different from the first wireless communication protocol.

17. The command module of claim 16, wherein the first wireless communication protocol is a protocol operable via magnetic induction and at or near 5 MHz and the second wireless communication protocol is a wireless communication protocol operable via modulation of electromagnetic radiation and at or near 2.4 GHz.

18. The command module of claim 14, wherein the processor is configured to detect that the external device is not in proximity to the command module, and in response, re-initiate operation in the first mode.

19. The command module of claim 18, wherein to detect that the external device is not in proximity to the command module, the processor is configured to determine that an inductive element of the external device is not sufficiently close to an inductive element of the command module.

* * * * *